United States Patent [19]
Eggli et al.

[11] 4,445,518
[45] May 1, 1984

[54] METHOD OF APPLYING AN AREAL FLEXIBLE ELECTRODE TO A SPOT OF THE BODY COVERED BY A PLASTIC CAST AS WELL AS A DEVICE FOR EXECUTING THIS METHOD

[75] Inventors: Danièle Eggli, Dübendorf; Dieter von Ow, Zürich; Gregor Hüni, Dübendorf, all of Switzerland

[73] Assignee: Hans Leuenberger, Wallisellen, Switzerland

[21] Appl. No.: 262,205

[22] Filed: May 8, 1981

[30] Foreign Application Priority Data
May 5, 1980 [CH] Switzerland ................. 3674/80

[51] Int. Cl.³ .............................................. A61N 1/04
[52] U.S. Cl. ..................................... 128/783; 128/802
[58] Field of Search ............... 128/82.1, 390, 783, 128/791–793, 798, 799, 802, 803

[56] References Cited
U.S. PATENT DOCUMENTS

| | | | |
|---|---|---|---|
| 1,989,282 | 1/1935 | Kimble et al. | 128/798 |
| 4,207,904 | 6/1980 | Greene | 128/798 |
| 4,267,840 | 5/1981 | Lazar et al. | 128/798 X |
| 4,317,457 | 3/1982 | Guillot | 128/783 |

FOREIGN PATENT DOCUMENTS 787477 9/1935 France .................. 128/798
1027350 5/1957 France .................. 128/82.1

Primary Examiner—Lee S. Cohen
Attorney, Agent, or Firm—Wood, Dalton, Phillips, Mason & Rowe

[57] ABSTRACT

For pulling an areal flexible electrode (4) between the inside surface of a plaster cast (2) and a member (1) of the body encased in a plaster cast (2), the plaster cast (2) is provided with at least one small hole (10) through which a draw wire is slid into the interior of the plaster cast (2) up to its front side opening (9). Thereupon the end of the draw wire is fastened on the electrode (4) so that said electrode can be pulled into the plaster cast (2) to a specified body spot by means of the draw wire. In order to achieve intimate contact of the surface of the electrode (4) with the body spot, the electrode (4) is provided on the opposite side with an elastic padding (6) which is supported on the inside surface of the plaster cast (2) in the draw-in position of the electrode (4). In a simple manner, the areal electrode (2) can thereby be put several times on the body spot covered by the plaster cast without the necessity of changing the plaster cast in a manner disadvantageous of the member of the body.

10 Claims, 3 Drawing Figures

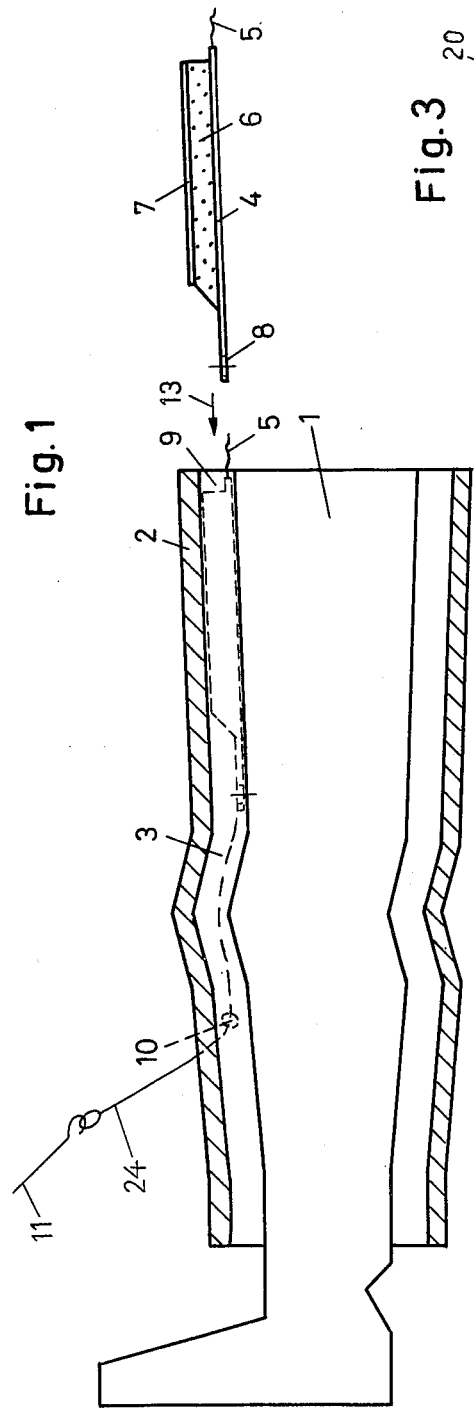
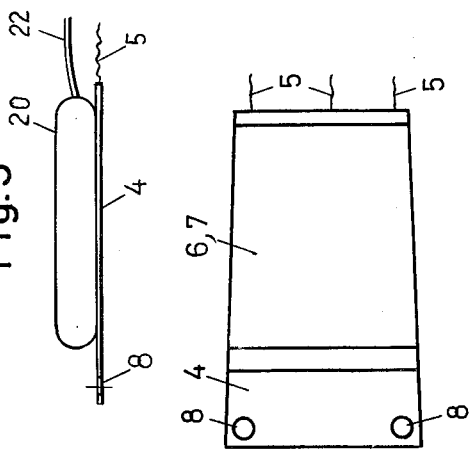
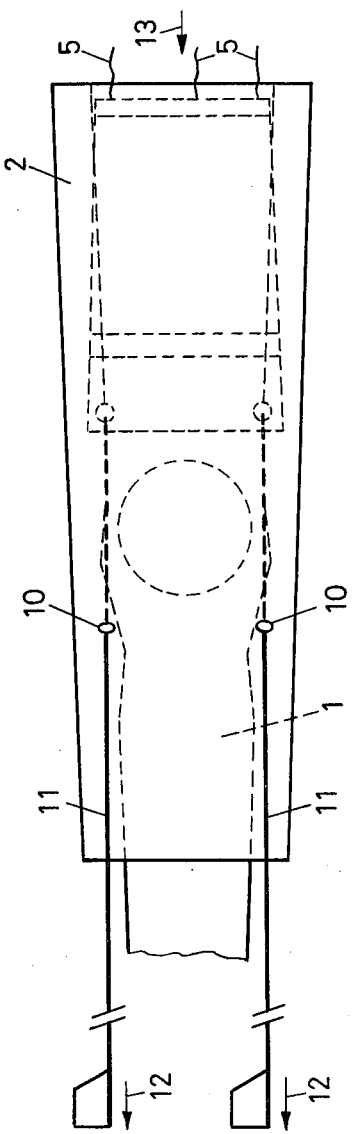
Fig. 1
Fig. 2
Fig. 3

METHOD OF APPLYING AN AREAL FLEXIBLE ELECTRODE TO A SPOT OF THE BODY COVERED BY A PLASTIC CAST AS WELL AS A DEVICE FOR EXECUTING THIS METHOD

The invention relates to a method for applying an areal flexible electrode to a spot of the body covered by a plaster cast as well as to a device for executing this method.

It has been known for a long time to apply alternating currents to the human body over the skin in order to obtain certain stimulating effects with the use of areal flexible electrodes which can be adjusted well to the respective part of the body. Especially in order to fight muscle atrophy or for the development of muscles, such a body treatment has proved to be favorable. In this respect the mentioned treatment of the body is desirable if a part of the body is provided with a plaster cast since muscle activity is made impossible because of the applied plaster cast and considerable muscle atrophy must be taken into account.

The application of stimulating currents by means of an areal electrode to body portions encased in a plaster cast, however, is confronted by the difficulty of putting the electrode on the respective spot of the body in an intimate contact and of removing it again from the spot of the body if this spot is covered by the plaster cast. On the one hand, the application of stimulating currents is supposed to take place at specified intervals over a rather long time; on the other hand, however, it is out of the question to leave the electrode continuously on the spot of the body.

The attempt has been made before to break a rather large opening out of the plaster cast and to put the areal electrode on the surface of the body through this opening. However, this procedure is confronted by the disadvantages of a considerable weakening of the plaster cast as well as by the impossibility to put the electrode on several body spots on the part of the body encased in the plaster cast.

The present invention has the problem to develop a method and a device by means of which an areal electrode can be put in intimate contact several times under the plaster cast with any spot of the body covered by the plaster cast without impairing the cast.

For the solution of said problem the method as defined in the invention has the characteristics stated in claim 1. Furthermore, the device as defined in the invention for executing the method is characterized by patent claim 4.

Embodiments of the method as defined in the invention and of the device for its execution are explained in the following and by means of the drawing.

FIG. 1 shows schematically a longitudinal section through a plaster cast with an areal electrode, FIG. 2 shows a top view of the plaster cast and the electrode of FIG. 1 with draw-in means for the electrode FIG. 3 is a section view through another embodiment of the areal electrode.

As it is illustrated schematically in FIG. 1 and 2, the thigh and the lower leg of a leg 1 are provided with a plaster cast encasing them. A certain time after the plaster cast has been put on, the cast because of changes of the body tissue and of the body muscles forms with the surface of the leg at least at some spots an interstice 3 which is not illustrated full scale in the figures.

An electrode 4 to be put on a body spot under the plaster cast has an areal design. It consists, for instance of two flexible foils of a synthetic material or of rubber between which a very fine metal braid is embedded which extends over the entire foil surfaces and is provided with connecting wires 5. The foils contain here an admixture of conducting carbon black so that they are electrically conducting. The surfaces of the films are smooth and water-repellent.

On one surface of the electrode 4 there is attached an elastic padding 6 which in the illustrated embodiment is a foam material plate covered with a smooth foil 7 of synthetic material. In place of a foam material plate, the electrode 4 can also be provided with an air cushion, especially with an air cushion 20 inflatable by way of a thin flexible hose 22. Furthermore, the electrode 4 has two holes or eyes 8 whose purpose is explained in the following.

In order to put the electrode 4 together with the elastic padding 6 into the interstice 3 on the body spot to be treated, the plaster cast 2 is provided later with two small holes 10 at a spot which in relation to that body spot is spaced away from the front side opening 9 of the plaster cast 2. An extended pull wire 11 is inserted into each of these holes 10 and slid along the inside surface of the plaster cast until its end comes out of the front side opening 9. The ends of the two pull wires 11, which, for instance, are hook-shaped, can now be hung into the holes or eyes 8 of the electrode 4. Thereupon the two pull wires 11 are drawn out of the holes 10 of the plaster cast 2 in the direction of the arrow 12 so that the electrode 4 is drawn into the interstice 9 as it is indicated by the arrow 13. The pull wires 11 are pulled here until the electrode 4 is in the position—illustrated by broken lines in the figures—relative to the body spot to be treated. Since here the electrode 4 is supported against the inside surface of the plaster cast 2 by way of the elastic padding 6, the opposite surface of the electrode bears uniformly and intimately on the leg 1. After the treatment has taken place, the electrode can again be pulled out of the plaster cast 2 by the connecting wires 5. Subsequently the pull wires 11 are unhooked again from the electrode 4 and pulled out of the hole 10.

In order to prevent the pull wires 11 from remaining inside the plaster cast 2 during the treatment, pull bands, for instance, textile pull bands 24, can also be used for the described drawing in of the electrode 4. For this purpose the pull bands 24 are either drawn in combined with the pushing in of the pull wires 11 through the holes 10 and then connected with the electrode 4 or pull bands fastened on the electrode 4 are drawn into the interior of the plaster cast 2 by the pull wires 11 which are pushed in and come out again of the opening 9 and are pulled to the outside again through the holes 10.

The design of the elastic padding 6 as an inflatable air cushion is especially advantageous. The electrode 4 and the non-inflated air cushion can then be drawn without great resistance into the interstice 3 between the plaster cast 2 and the leg 1. The subsequent inflating of the air cushion effects the required intimate contact of the electrode 4 on the surface of the leg 1.

The present invention makes possible in a simple and arbitrarily repeatable manner the placing of the electrode on a body spot covered by a plaster cast without the necessity of changing the effect and the position of the plaster cast in any way relative to the body spot.

We claim:

1. The method for applying an areal flexible electrode on a spot of the body covered by a plaster cast comprising:
    drawing the electrode in along the inside surface of the plastic case to position said electrode on said body spot; and
    elastically supporting said electrode at the respective body spot against the inside surface of the plaster cast.

2. The method of claim 1 wherein the electrode is drawn in by sliding a wire-like draw-in hook through at least one hole in the plaster cast along the inside surface of said plaster cast to an end opening thereof, connecting said hook to said electrode, and pulling said hook to draw the electrode in under the plaster cast.

3. The method of claim 1 wherein the electrode is drawn in by sliding a wire-like draw-in hook on which a pull band is fastened through at least one hole in the plaster cast along the inside surface of said plaster cast to an end opening thereof, connecting said pull band to said electrode, removing said hook, and pulling said pull band to draw the electrode in under the plaster cast.

4. A device for stimulating a spot on the body encased by a plaster cast comprising:
    a flexible areal electrode adapted to be deposed between the cast and the body, said electrode having one conductive surface defining an electrode for contacting and stimulating said body spot, another surface to engage the inside of said cast and means between said surfaces acting against the cast to urge the conductive surface against the body spot;
    wires connected to said electrode conductive surface to transmit stimulating electric current thereto; and
    means for locating said areal electrode within said cast against said body spot.

5. The device of claim 4 wherein the means between the electrode surfaces consists of foam material.

6. The device of claim 5, wherein said another surface engaging the inside of said cast is a smooth foil of synthetic material.

7. The device of claim 4 wherein the means between the electrode surfaces is an air cushion.

8. The device of claim 7 wherein the air cushion is inflatable.

9. The device as defined in claim 4 wherein said one surface of electrode is an electrically conducting plate of flexible material with a metal conductor embedded therein.

10. The device of claim 4 wherein said locating means is a filament adapted to extend along the inside of the cast and attached to said areal electrode, whereby pulling of said filament moves said areal electrode inside said cast.

* * * * *